(12) United States Patent
Shimbo et al.

(10) Patent No.: US 8,879,057 B2
(45) Date of Patent: Nov. 4, 2014

(54) SPECTRAL CHARACTERISTIC ACQUIRING APPARATUS, SPECTRAL CHARACTERISTIC ACQUIRING METHOD AND IMAGE EVALUATING APPARATUS

(75) Inventors: Kohei Shimbo, Kanagawa (JP); Naohiro Kamijo, Kanagawa (JP); Yoichi Kubota, Tokyo (JP); Manabu Seo, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 294 days.

(21) Appl. No.: 13/559,982

(22) Filed: Jul. 27, 2012

(65) Prior Publication Data

US 2013/0063723 A1 Mar. 14, 2013

(30) Foreign Application Priority Data

Sep. 12, 2011 (JP) .................................. 2011-198374

(51) Int. Cl.
| | | |
|---|---|---|
| *G01J 3/00* | (2006.01) | |
| *G01J 3/40* | (2006.01) | |
| *G01J 3/28* | (2006.01) | |
| *G01J 3/52* | (2006.01) | |
| *G01J 3/04* | (2006.01) | |
| *G01J 3/50* | (2006.01) | |
| *H04N 1/60* | (2006.01) | |
| *B41F 33/00* | (2006.01) | |
| *G01N 21/86* | (2006.01) | |

(52) U.S. Cl.
CPC .. *G01J 3/524* (2013.01); *G01J 3/04* (2013.01); *G01J 3/28* (2013.01); *G01J 3/502* (2013.01); *H04N 1/6033* (2013.01); *B41F 33/00* (2013.01); *G01N 21/86* (2013.01)
USPC ............ 356/300; 356/305; 356/326; 356/328

(58) Field of Classification Search
USPC .................................. 356/300–334, 402–425
See application file for complete search history.

(56) References Cited

U.S. PATENT DOCUMENTS

| | | | |
|---|---|---|---|
| 6,975,949 B2 | 12/2005 | Mestha et al. | |
| 7,057,723 B2 | 6/2006 | Klock et al. | |
| 2004/0061855 A1* | 4/2004 | Klock et al. | ................... 356/328 |

(Continued)

FOREIGN PATENT DOCUMENTS

| | | |
|---|---|---|
| JP | 2005-315883 | 11/2005 |
| JP | 2010-256324 | 11/2010 |
| WO | WO 2005/124302 A1 | 12/2005 |

OTHER PUBLICATIONS

Extended European Search Report dated Jan. 2, 2013.

(Continued)

*Primary Examiner* — Kara E Geisel
*Assistant Examiner* — Hina F Ayub
(74) *Attorney, Agent, or Firm* — IPUSA, PLLC

(57) ABSTRACT

A spectral characteristic acquiring apparatus is provided which includes: an area dividing part; a spectrum separating part; a light receiving part; and a calculating part, wherein the calculating part includes a transformation matrix storing part that stores a transformation matrix used for calculating the spectral characteristic corresponding to electrical signals of a first diffraction pattern group including two or more adjacent diffraction patterns, and a spectral characteristic calculating part that calculates, based on the electrical signals of the first diffraction pattern group and the corresponding transformation matrix, the spectral characteristic at the locations of the image carrying medium corresponding to the apertures of the first diffraction pattern group.

8 Claims, 12 Drawing Sheets

(56) References Cited

U.S. PATENT DOCUMENTS

| | | |
|---|---|---|
| 2011/0063615 A1 | 3/2011 | Shimbo et al. |
| 2011/0106472 A1 | 5/2011 | Seo et al. |
| 2011/0222056 A1 | 9/2011 | Seo et al. |
| 2011/0299104 A1 | 12/2011 | Seo et al. |
| 2011/0317149 A1 | 12/2011 | Shimbo et al. |

OTHER PUBLICATIONS

Tsumura et al. "Estimation of Spectral Reflectances from Multi-Band Images by Multiple Regression Analysis", *Kougaku* vol. 27, No. 7, pp. 384-391, 1998.

\* cited by examiner

FIG.2
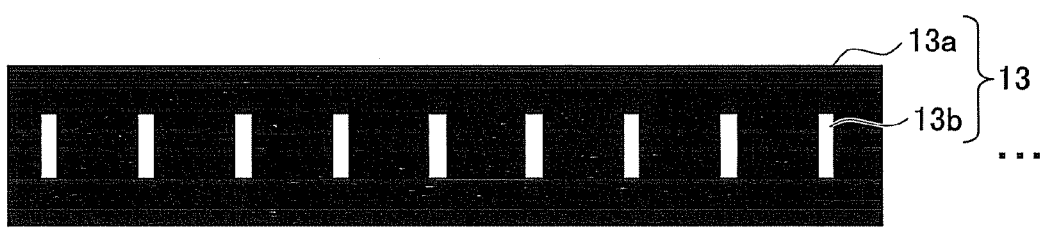
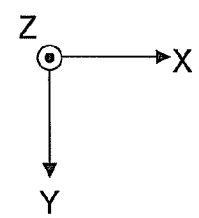

SPECTRAL CHARACTERISTIC ACQUIRING APPARATUS, SPECTRAL CHARACTERISTIC ACQUIRING METHOD AND IMAGE EVALUATING APPARATUS

FIELD

The invention is related to a spectral characteristic acquiring apparatus and a spectral characteristic acquiring method for acquiring a spectral characteristic of a target object, and an image evaluating apparatus which includes the spectral characteristic acquiring apparatus.

BACKGROUND

Recently, even in a field of production printing, digitization of sheet-fed printing presses and printers for continuous slip/form paper have been promoted, and many products of an electrophotograph type, an inkjet type, etc., have been introduced commercially. Demands on high quality and color reproduction stability of printed images by these apparatuses become higher.

In order to improve the color reproduction stability, a calibration of the apparatus is performed by measuring colors of the printed material with a spectrometer, or a printing condition is controlled by feeding back color information. According to the spectrometer of prior art, the measurement is performed at a point in a region of interest to print an arbitrary color chart, and then color measuring is performed based on the color chart. It is desirable that these techniques are applied to the image as a whole in order to compensate for variations of the image within a page or between pages. There are products which perform measurements at plural points by moving a single spectrometer; however, it is difficult to apply such a technique to the in-line measurements for high-speed apparatuses used for production printing, etc.

Japanese Laid-open Patent Publication No. 2005-315883 discloses a technique for the in-line color measurement over a full width of the image in which the image is illuminated over its full width with a light source having different frequency bands and the reflected light is acquired to obtain a spectral characteristic over the full width. However, according to the technique disclosed in Japanese Laid-open Patent Publication No. 2005-315883, the reflected light is received while a color of the illumination is changed by time division, and thus it is difficult to acquire the signal of the reflected light associated with the same point, resulting in failing to measure the color with high accuracy.

Further, Japanese Laid-open Patent Publication No. 2010-256324 discloses a technique for acquiring light intensity signals of respective diffracted images on a wavelength band basis with plural pixels of a one-dimensional array sensor wherein the reflected light from the target object is limited spatially with an aperture array such as a pin-hole array, and then the spectrum separation of the reflected light forms plural diffracted images on the one-dimensional array sensor. According to the technique disclosed in Japanese Laid-open Patent Publication No. 2010-256324, plural signals with different spectral characteristics can be acquired at a time and precise spectral characteristics at the respective locations corresponding to the respective apertures can be acquired.

If the target object in the printed image is a user image, for example, it is desirable that the measurement is performed with a high resolution such that colors even in a narrow range can be evaluated. On the other hand, if the target object in the printed image is a color chart, for example, it is desirable that an average color within a range of a color sample is measured with high accuracy but a high spatial resolution is not necessary.

According to the prior art, in order to perform the measurement with a spatial resolution adequate for the target object, it is necessary to replace the aperture array such as a pin-hole array as necessary according to the target object, for example in the case of the technique disclosed in Japanese Laid-open Patent Publication No. 2010-256324.

However, in this case, plural types of the aperture arrays having different intervals between the apertures become necessary, which requires much effort. Further, there may be a concern that a relative positional relationship between diffraction patterns corresponding to the respective apertures of the aperture array and a one-dimensional array sensor is varied by the replacement of the aperture array. If the relative positional relationship is varied, there is a problem that the spectral characteristics of the respective signals are changed and thus the calibration is necessary every time when the aperture array is replaced, thereby complicating the measurements.

The present invention is made in consideration of the matters described above, and an object of the present invention is to provide a spectral characteristic acquiring apparatus capable of acquiring spectral characteristics at plural positions with a spatial resolution adequate for a target object.

SUMMARY

In order to solve the problem, according to the present invention, a spectral characteristic acquiring apparatus is provided which includes: an area dividing part that divides a reflected light beam into plural areas with plural apertures, the reflected light beam being generated based on a light beam radiated from a light radiating part to an image carrying medium; a spectrum separating part that performs a spectrum separation of the reflected light beams divided by the area dividing part to form plural diffraction patterns; a light receiving part that receives the diffraction patterns formed by the spectrum separating part with plural pixels to convert the received diffraction patterns into electrical signals; and a calculating part that calculates, based on the electrical signals, a spectral characteristic that indicates a ratio of a light amount of the reflected light beam at plural locations of the image carrying medium, wherein the calculating part includes a transformation matrix storing part that stores a transformation matrix used for calculating the spectral characteristic corresponding to the electrical signals of a first diffraction pattern group including two or more adjacent diffraction patterns, and a spectral characteristic calculating part that calculates, based on the electrical signals of the first diffraction pattern group and the corresponding transformation matrix, the spectral characteristic at the locations of the image carrying medium corresponding to the apertures of the first diffraction pattern group.

BRIEF DESCRIPTION OF DRAWINGS

FIG. 2 is a plan view for schematically illustrating a hole array according to a first embodiment.

DESCRIPTION OF EMBODIMENTS

Figure 1:
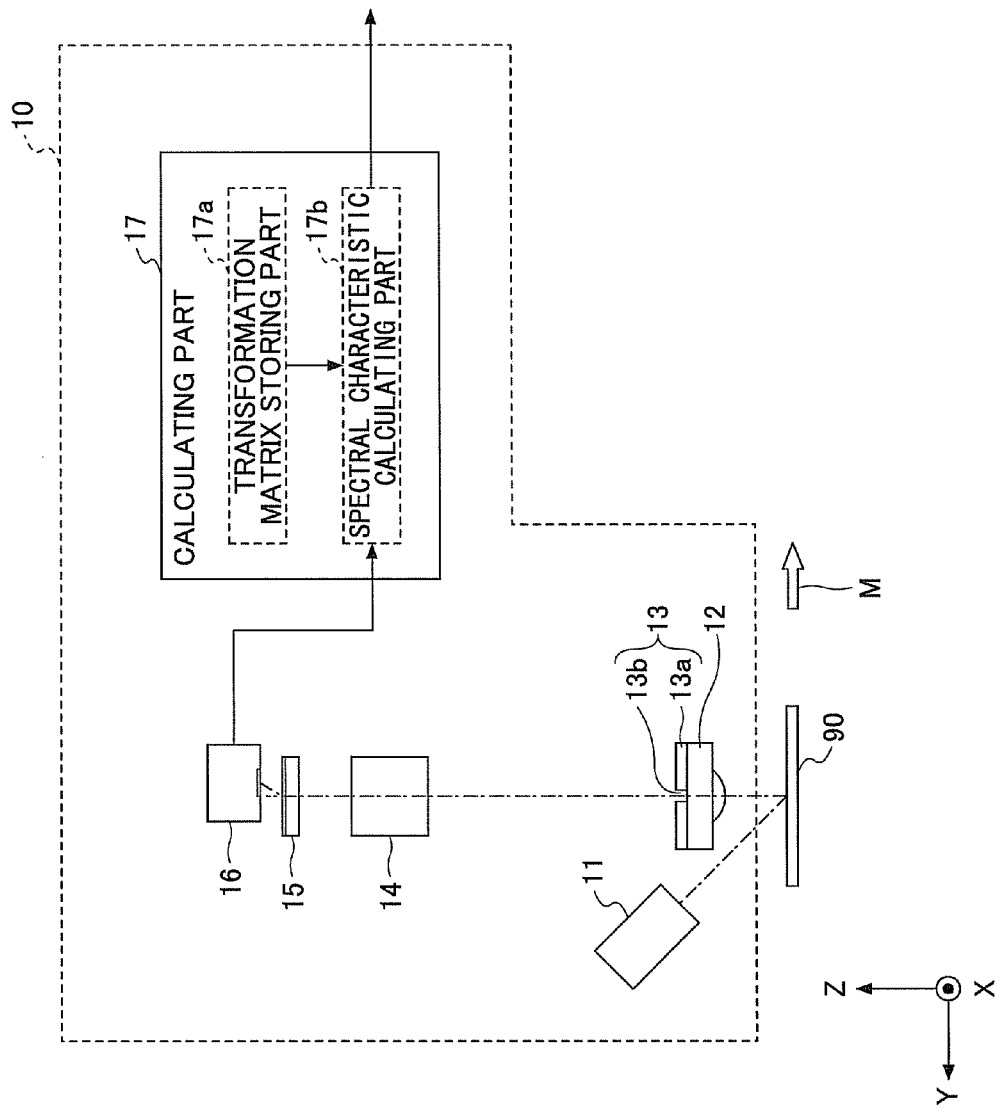
FIG. 1 is a diagram for schematically illustrating a spectral characteristic acquiring apparatus according to a first embodiment.

In the following, embodiments will be described by referring to the accompanying drawings. It is noted that in the respective drawings, the same elements are indicated by the same reference numerals, and explanation may be omitted to avoid overlaps.

First Embodiment

FIG. 1 is a diagram for schematically illustrating a spectral characteristic acquiring apparatus according to a first embodiment. In the following, expressions "X-direction", "Y-direction" and "Z direction" indicate axis directions illustrated in the drawings. Further, in the application, the term "spectral characteristic" indicates a light amount of diffused reflection light expressed as a function of wavelength, and the spectral characteristic includes a spectral reflection factor. It is noted that the spectral reflection factor expresses a ratio of the light amount of diffused reflection light from a target object to a light amount of diffused reflection light from a reference plate (a white plate, for example) as a function of wavelength.

Referring to FIG. 1, the spectral characteristic acquiring apparatus 10 mainly includes a line illumination light source 11, an imaging optical system 12, a hole array 13, an imaging optical system 14, a spectrum separating part 15, and a line sensor and a calculating part 17. An image carrying medium which is a target object to be measured is indicated by a reference numeral 90. An image is formed on a predetermined area of the image carrying medium 90. The image carrying medium 90 is a sheet of a printed material, etc., for example, and may be conveyed at a constant speed in a direction indicated by an arrow M (Y-direction) in FIG. 1.

It is noted that, in the following, regular reflection light indicates reflected light which is reflected in an opposite direction with respect to an incident direction and at the same angle as an incident angle of illumination light radiated from the line illumination light source 11 to the image carrying medium 90. In other words, regular reflection light is the reflected light whose reflection angle is π-θ if the incident angle is θ. Further, the diffused reflection light indicates the reflected light other than the regular reflection light.

The line illumination light source 11 has a function of radiating the light to an area of the image carrying medium 90 which extends in a line form in a length direction (X-direction) of the image carrying medium 90. The line illumination light source 11 may be a white color LED (Light Emitting Diode) array which has strength over substantially all the region of visible light, for example. The line illumination light source 11 may be a fluorescent tube such as a cold-cathode tube and a lamp light source, etc. However, it is preferred that the line illumination light source 11 emits the light having a range of a wavelength required for the spectrum separation and be capable of uniformly radiating an area to be measured as a whole (one line in X-direction on the image carrying medium 90). It is noted that the line illumination light source 11 is a representative example of a light radiating part according to the invention.

A collimating lens, which has a function of collimating (making substantially parallel rays) or collecting the light emitted from the line illumination light source 11 to implement line-shaped illumination, on a light path from the line illumination light source 11 to the image carrying medium 90.

The imaging optical system 12 has a function of imaging the diffused reflection light in a normal direction (Z direction) of the light radiated to the image carrying medium 90 on apertures 13b of the hole array 13. For example, the imaging optical system 12 may be a condenser lens array in which plural lenses are arranged in X-direction, etc.

However, the diffused reflection light is not necessarily imaged precisely on an aperture array of the hole array 13, and thus a defocused status or an infinite system may be possible. The imaging optical system 12 may include a refractive index profile type lens array such as a Selfoc lens array, a micro lens array or a mirror. It is noted that the imaging optical system 12 is a representative example of a first imaging part according to the present invention.

As illustrated in FIG. 2, the hole array 13 has the aperture array formed on a light blocking member 13a such that plural apertures 13b are arranged in a line. The hole array 13 divides the diffused reflection light radiated thereto via the imaging optical system 12 into plural areas. In the following, dividing into plural areas is also simply referred to as an area division. In the hole array 13, the apertures 13b having substantially the same shape are arranged in a line in X-direction and spaced with substantially the same interval to form the aperture array.

The hole array 13 may be formed of a transparent member such as a glass on which a metal film or a black resin is applied as a light blocking member 13a in which the aperture array is formed partly, or the hole array 13 may be a member in which the aperture array are formed in a slit form in the light blocking member 13a which is made of a metal thin plate, etc. It is noted that in FIG. 2 the apertures 13b of the hole array 13 have a rectangular shape; however, the shape is arbitrary. For example, the apertures 13b have an ellipse shape, and circle shape, or other more complicated shapes.

With the hole array 13, the diffused reflection light from the target object is divided into the areas by the aperture array of the hole array 13, thereby blocking an undesired portion of the light. In this way, only the light on a focal plane, which passes through the respective apertures 13b of the aperture array, is detected, and thus the intrusion of the reflected light from adjacent areas can be reduced. It is noted that the hole array 13 is a representative example of an area dividing part according to the invention.

The light beams related to images obtained by the area division on the hole array 13 are collected and are radiated to the spectrum separating part 15. In other words, the imaging optical system 14 collects the diffused reflection light passing through the aperture array to form an image on the spectrum separating part 15. It is noted that the imaging optical system 14 is a representative example of a second imaging part according to the present invention.

The spectrum separating part 15 has a function of forming the diffraction patterns corresponding to the respective apertures 13b of the aperture array by separating the diffused reflection light collected by the imaging optical system 14 after the area division with the aperture array of the hole array 13 into spectrums to propagate in different directions according to the wavelength. The spectrum separating part 15 may include a prism, a transmission grating or a combination thereof, for example.

A line sensor 16 has a function of receiving light of the respective diffraction patterns formed by the spectrum separating part 15 with plural pixels to acquire the light amount on a predetermined wavelength basis, and converting the acquired light amounts into electric signals. The line sensor 16 may include a MOS (Metal Oxide Semiconductor Device), CMOS (Complimentary Metal Oxide Semiconductor Device), CCD (Charge Coupled Device), CIS (Contact Image Sensor), etc., for example. It is noted that the line sensor 16 is a representative example of a light receiving part according to the invention.

Figure 3:
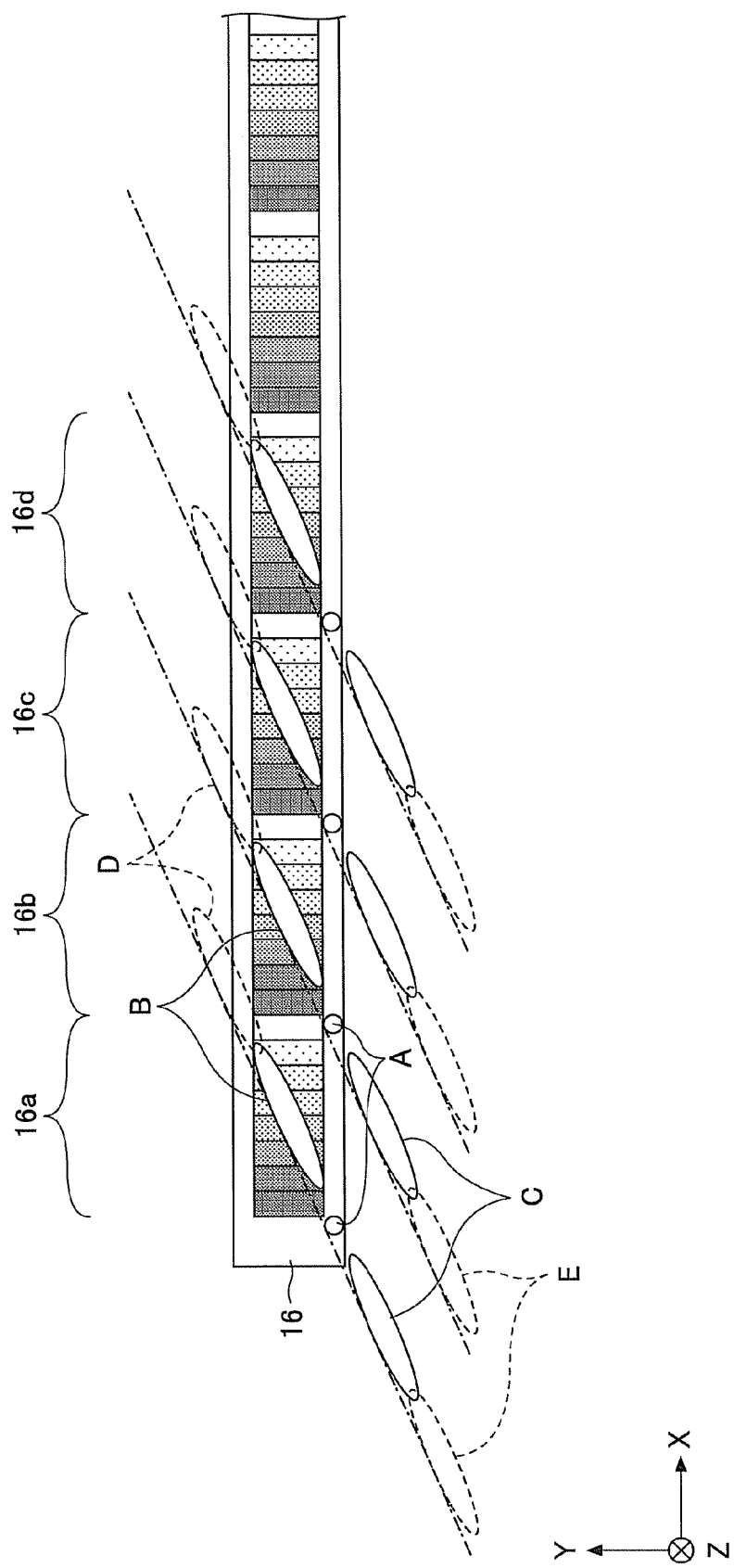
FIG. 3 is a diagram (No. 1) for illustrating a status of respective diffraction patterns incident on a line sensor, viewed from a side of an incident plane.

FIG. 3 is a diagram (No. 1) for illustrating a status of respective diffraction patterns incident on the line sensor, viewed from a side of an incident plane. Referring to FIG. 3, the line sensor 16 has a pixel configuration in which plural pixels, which have long light receiving areas in a Y-direction, are arranged in a line in an X-direction. The line sensor 16 forms a spectral sensor array in which spectral sensors 16a, 16b, 16c, 16d, etc., each of which includes N pixels neighboring in an X-direction as a group, are arranged in an X-direction.

The spectral sensors 16a, 16b, 16c, 16d, etc., include N pixels neighboring in an X-direction which receive the light of different spectral characteristics. In the example illustrated in FIG. 3, N is 8 (there may be a case where an invalid pixel is included in the eight pixels).

On the line sensor 16 are formed only the ± first order diffraction patterns B of the apertures 13b of the hole array 13. Unnecessary non-diffraction patterns A ($0^{th}$ order diffraction patterns), − first order diffraction patterns C, + second-order diffraction patterns D, − second-order diffraction patterns E, etc., are formed at locations away from the pixels of the line sensor 16. The respective apertures 13b of the hole array 13 correspond to the respective first-order diffraction patterns (the respective spectral sensors) on the line sensor 16 such that one of the apertures 13b has an image-forming relationship with N pixels of the corresponding spectral sensor. Thus, it is possible to precisely acquire the measurement locations of the image carrying medium 90 to be measured.

By appropriately setting a diffraction axis direction of the spectrum separating part 15, a pitch of the diffraction grating, a distance between the spectrum separating part 15 and the line sensor 16, etc., it is possible to direct only the + first-order diffraction patterns diffracted in an inclined direction as illustrated in FIG. 3 to the neighboring pixels of the line sensor 16 while directing the non-diffraction patterns A ($0^{th}$ order diffraction patterns) and the diffraction patterns with orders other than a desired order to the locations away from the pixels of the line sensor 16. With this arrangement, plural light strength signals with different spectral characteristics can be obtained with respect to the respective first-order diffraction patterns B. In the following the + first-order diffraction patterns B are also simply referred to as the diffraction patterns.

The diffused reflection light beams with the respective wavelengths received by the line sensor 16 are subject to optoelectronic conversion according to the received light amount, and they are digitized, for example, before being transferred to the calculating part 17. After spectral information of the one-dimensional line is transferred to the calculating part 17, the image carrying medium 90 to be measured is moved in the direction indicated by the arrow M in FIG. 1 with respect to the spectral characteristic acquiring apparatus 10, and then spectral information of the next one-dimensional line is acquired by the line sensor 16 and transferred to the calculating part 17. By repeating such operations, the color measuring over the full width of the image is enabled.

It is noted that the optical system illustrated in FIG. 1 is a so-called 45/0 optical system in which the illumination light emitted from the line illumination light source 11 is transmitted to the image carrying medium 90 with an incident angle of substantially 45 degrees, and the line sensor 16 receives the light diffused and reflected at the image carrying medium 90 in a direction perpendicular to the image carrying medium 90. However, the configuration of the optical system is not limited to the optical system illustrated in FIG. 1. For example, the illumination light emitted from the line illumination light source 11 is transmitted to the image carrying medium 90 with an incident angle of 90 degrees, and the line sensor 16 receives the light diffused and reflected at the image carrying medium 90 in a direction which forms an angle of 45 degrees with respect to the image carrying medium 90.

Here, a way of calculating the spectral characteristic (spectral reflection factor) by the calculating part 17 is described. The calculating part 17 has a function of calculating the spectral characteristics at plural locations of the image carrying medium 90 based on the electric signals output from the spectral sensors 16a, 16b, 16c, 16d, etc. The calculating part 17 operates such that "a" adjacent spectral sensors ("a" is a natural number more than or equal to 2, hereinafter) are handled as a spectral unit. In other words, the calculating part 17 operates such that "a" adjacent diffraction patterns are handled as a diffraction pattern group.

The calculating part 17 includes a transformation matrix storing part 17a and a spectral characteristic calculating part 17b. The transformation matrix storing part 17a has a function of storing transformation matrixes. Each transformation matrix is prepared for each diffraction pattern group, and each diffraction pattern group includes "a" adjacent diffraction patterns. Matrixes are used for calculating the spectral characteristics from the electrical signals corresponding to the respective diffraction pattern groups. The spectral characteristic calculating part 17b has a function of calculating, based on the electrical signals of the respective diffraction pattern groups and the corresponding transformation matrixes, the spectral characteristics at the locations of the image carrying medium corresponding to the adjacent "a" apertures 13b of the aperture array.

The calculating part 17 includes a CPU, a ROM, a main memory, etc., for example, and the functions of the calculating part 17 can be implemented when programs stored in the ROM are read out from the main memory and then executed by the CPU. However, a part or all of the calculating part may be implemented by only hardware resources. Further, the calculating part 17 may include plural apparatuses which are physically separated.

Figure 4:
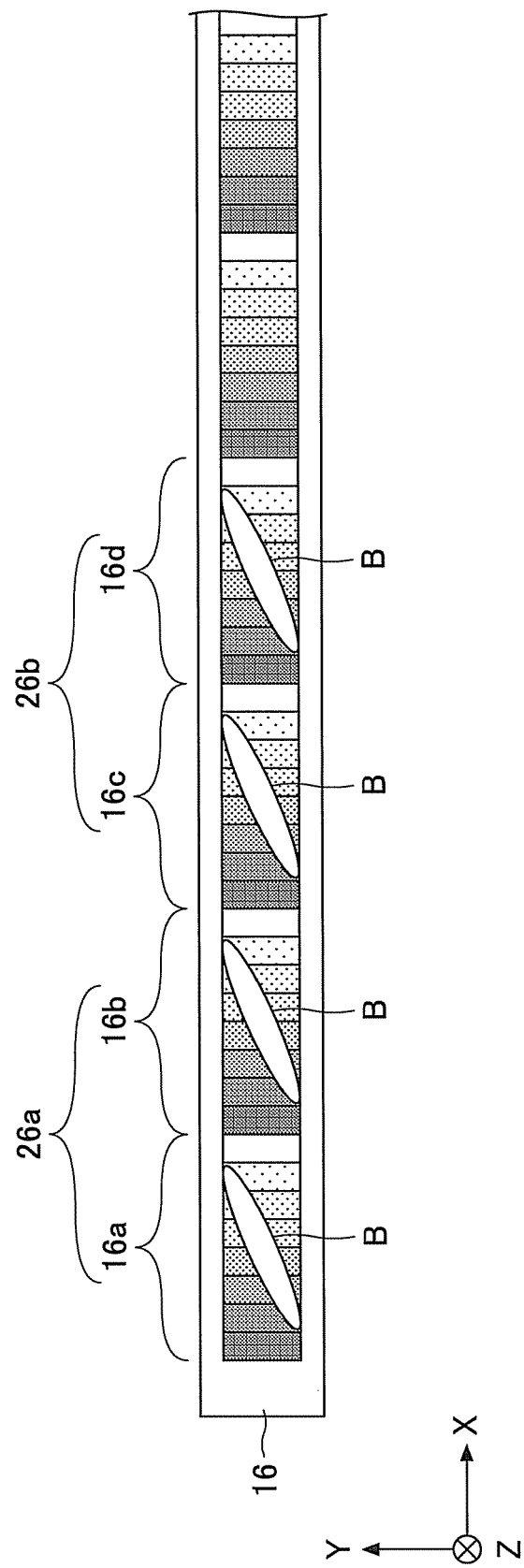
FIG. 4 is a diagram (No. 1) for illustrating an example of a spectral unit.

FIG. 4 is a diagram (No. 1) for illustrating an example of a spectral unit. In FIG. 4, two adjacent spectral sensors 16a and 16b are regarded as a spectral unit 26a. Further, two adjacent spectral sensors 16c and 16d are regarded as a spectral unit 26b. In other words, two diffraction patterns adjacent to each other on the line sensor 16 are regarded as a diffraction pattern group. It is noted that in FIG. 4 only the first-order diffraction patterns B are illustrated for the sake of convenience.

Figure 5:
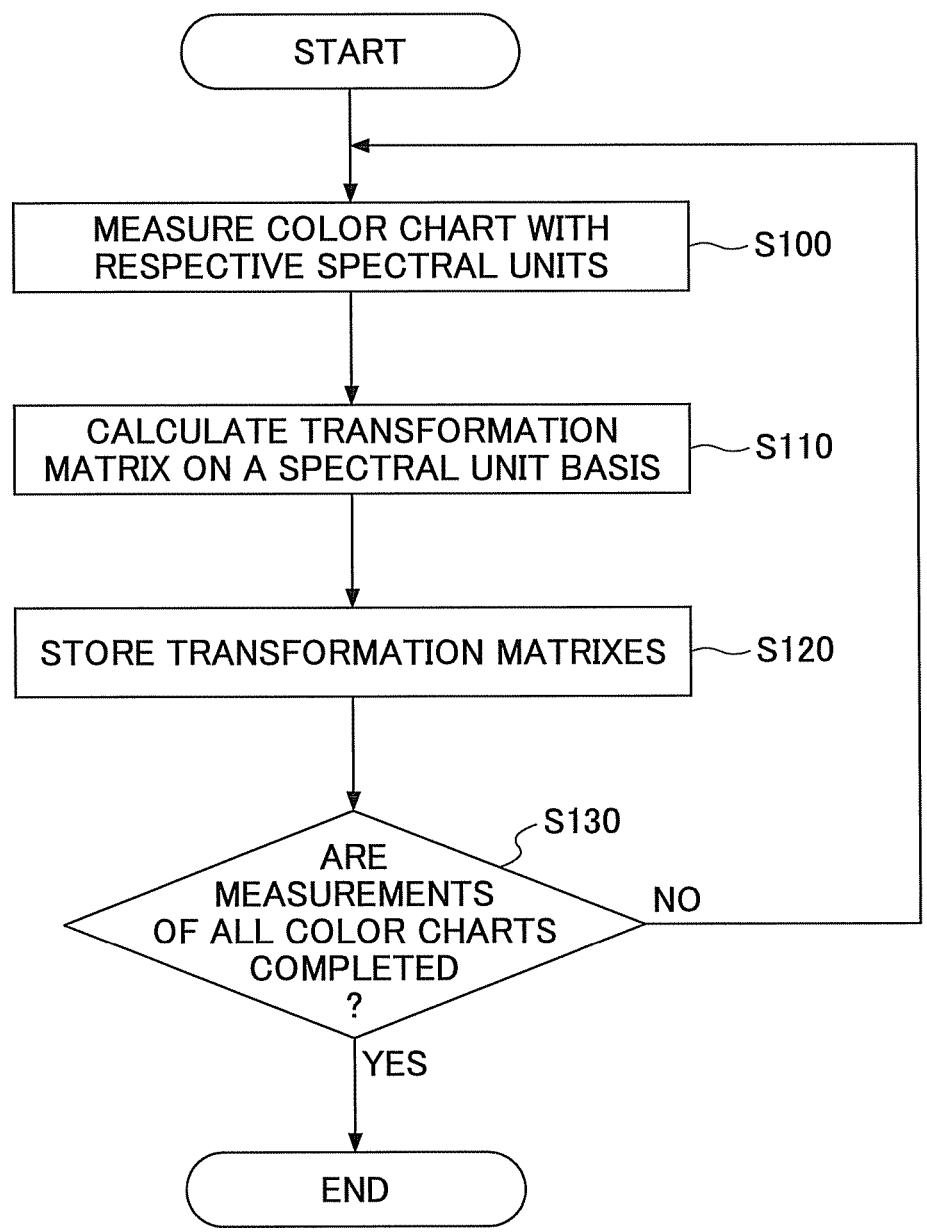
FIG. 5 is a flowchart of an example of a calibration process.
Figure 6:
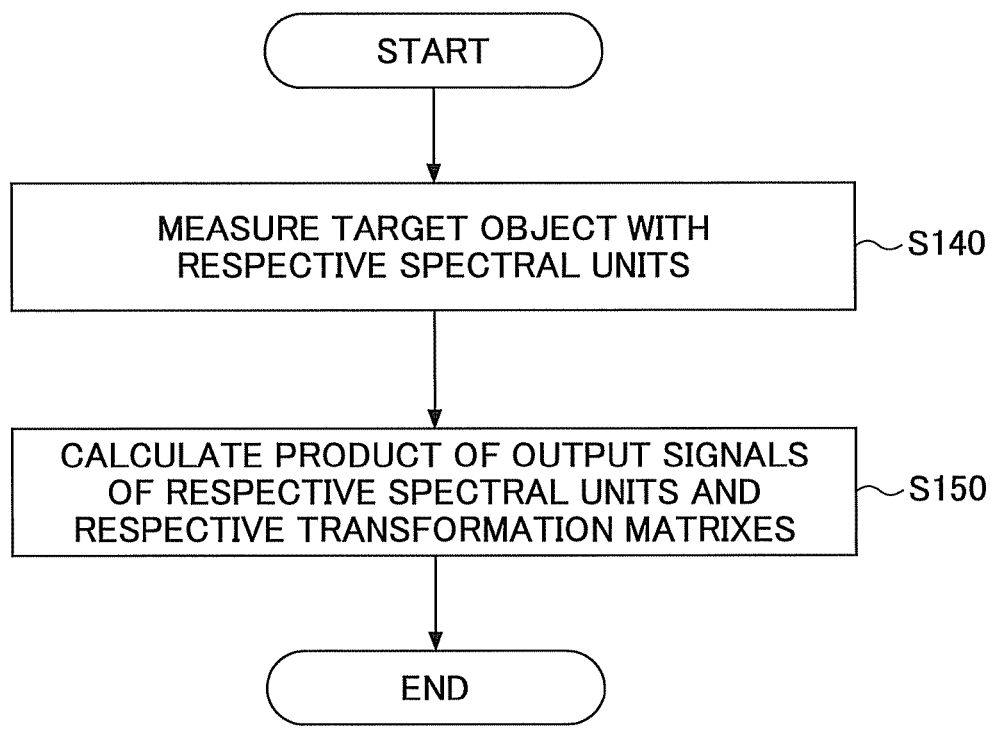
FIG. 6 is a flowchart of an example of a measurement process.

The calculating part 17 acquires the spectral characteristics of the respective spectral units (spectral units 26a and 26b, in this example) via a calibration process and a measurement process. FIG. 5 is a flowchart of an example of a calibration process. FIG. 6 is a flowchart of an example of a measurement process.

At first, the calibration process of steps 100 through 130 is performed. In step 100, plural color charts (color charts 1 through "n", where "n" is a natural number more than or equal to 2) whose spectral reflection factors are known are prepared as the image carrying media 90. The color chart 1 is measured by the respective spectral units (spectral units 26a and 26b, in this example) and the electric signals output from the spectral units are transferred to the spectral characteristic calculating part 17b.

It is noted that the color chart is a standard reference material for the purpose of color representation, and is also referred to as a color chip. The color chart may be a standard color chart which is in conformity with JIS-Z-8721, etc., for example. The color charts are measured with a spectrometer as a reference and the spectral reflection factors are known, for example.

In step 110, the spectral characteristic calculating part 17b calculates, based on the electric signals output from the spectral units, the transformation matrix for converting the electric signals into the spectral reflection factors by performing, on a spectral unit basis, a multiple regression analysis in which the known spectral reflection factors are used as response variables and the electric signals are used as predictor variables. In step 120, the transformation matrixes of the respective spectral units calculated in step 110 are stored in the transformation matrix storing part 17a.

Here, the transformation matrix is described in more detail. A row vector r, in which the spectral reflection factors of the respective wavelength bands (10 nm intervals between 400 nm and 700 nm, 31 spectral reflection factors, for example) are stored, is expressed by a formula (1) using a row vector v, in which electrical signals vi (I=1 through N) output from the N pixels of the spectral sensor are stored, and the transformation matrix G.

$$r = Gv \quad \text{formula (1)}$$

The transformation matrix G is determined by minimizing square norm of error with a least squares method based on a matrix R, in which spectral distributions for "n" color charts whose spectral distributions are known in advance are stored, and a matrix V, in which the vectors v obtained when the "n" color charts are measured by the spectral characteristic acquiring apparatus 10 are stored, as expressed by formulas (2) through (4).

$$R = [r1, r2, \ldots, rn] \quad \text{formula (2)}$$

$$V = [v1, v2, \ldots, vn] \quad \text{formula (3)}$$

$$e = \|R - GV\|^2 \rightarrow \min \quad \text{formula (4)}$$

The transformation matrix G, which is a regression coefficient matrix of a regression formula from V to R using V as response variables and R as predictor variables, is calculated as a formula (5) using a generalized inverse matrix of Moore-Penrose which gives a minimum norm least squares solution of the matrix V.

$$G = RV^T(VV^T)^{-1} \quad \text{formula (5)}$$

Here, a numerical superscript T indicates a transpose of a matrix, and a numerical superscript -1 indicates an inverse matrix. If the transformation matrix G thus determined is stored in the transformation matrix storing part 17a, a spectral distribution r of an arbitrary target object can be estimated by taking a product of the transformation matrix G and the electric signals vi at the time of the actual measurement. The matrix G can be determined on a spectral sensor basis or on a spectral unit basis, which spectral unit includes plural adjacent spectral sensors.

In step 130, it is determined whether the measurements of all the color charts (from the color chart 1 to the color chart n) are completed. If not (in the case of "NO"), the processes of steps 100 through 120 are repeated. If the measurements of all the color charts (from the color chart 1 to the color chart n) are completed (in the case of "YES"), the calibration process ends. In this way, the transformation matrix can be calculated based on the known spectral reflection factors and the spectral reflection factors measured by the spectral characteristic acquiring apparatus 10 with respect to the color charts on a spectral unit (spectral units 26a and 26b, in this example) basis. It is noted that the calibration process may be performed only once.

Next, the measurement process of steps 140 and 150 illustrated in FIG. 6 is performed. In step 140, the image carrying medium 90 which is the target object to be measured is prepared. Then, the image carrying medium 90, which is the target object to be measured, is measured by the respective spectral units and the electrical signals output from the spectral units are transferred to the spectral characteristic calculating part 17b. In step 150, the spectral characteristic calculating part 17b calculates products of the electrical signals output from the spectral units and the transformation matrixes of the corresponding spectral units stored in the transformation matrix storing part 17a to calculate the spectral reflection factors of the spectral units. In this way, the spectral reflection factors of the spectral units can be acquired.

In this way, according to the first embodiment, two adjacent spectral sensors are regarded as a spectral unit, and the transformation matrixes of the spectral units are calculated in advance by the calibration process. Then, in the measurement process, the spectral reflection factors of the spectral units are acquired by multiplying the electrical signals output from the spectral units by the transformation matrixes of the corresponding spectral units calculated in advance by the calibration process. With this arrangement, the acquired spectral reflection factor distribution is an average of spectral reflection factor distributions of light fluxes passing through two adjacent apertures of the hole array 13 in FIG. 1.

For example, if the target object is a part of the color chart in the printed image, the spectral reflection factors are substantially the same in the part of the color chart. In such a case, by applying the spectral characteristic acquiring method according to the first embodiment, an average spectral reflection factor over a wide range can be acquired with high stability.

Further, since the measurement is performed such that plural adjacent spectral sensors are regarded as a spectral unit, the number of the signals used for calculating the spectral reflection factor is increased. For example, the influence by random noise, which is generated in performing the optoelectronic conversion of the output signals of the line sensor, is reduced, thereby obtaining the spectral reflection factor distribution with increased stability.

It is noted that more than three adjacent spectral sensors may be regarded as a spectral unit.

First Variant of the First Embodiment

According to a first variant of the first embodiment, an example is illustrated in which the same spectral sensor is shared among the spectral units. It is noted that in the first variant of the first embodiment an explanation for the components which are the same as those in the previously described embodiment is omitted.

Figure 7:
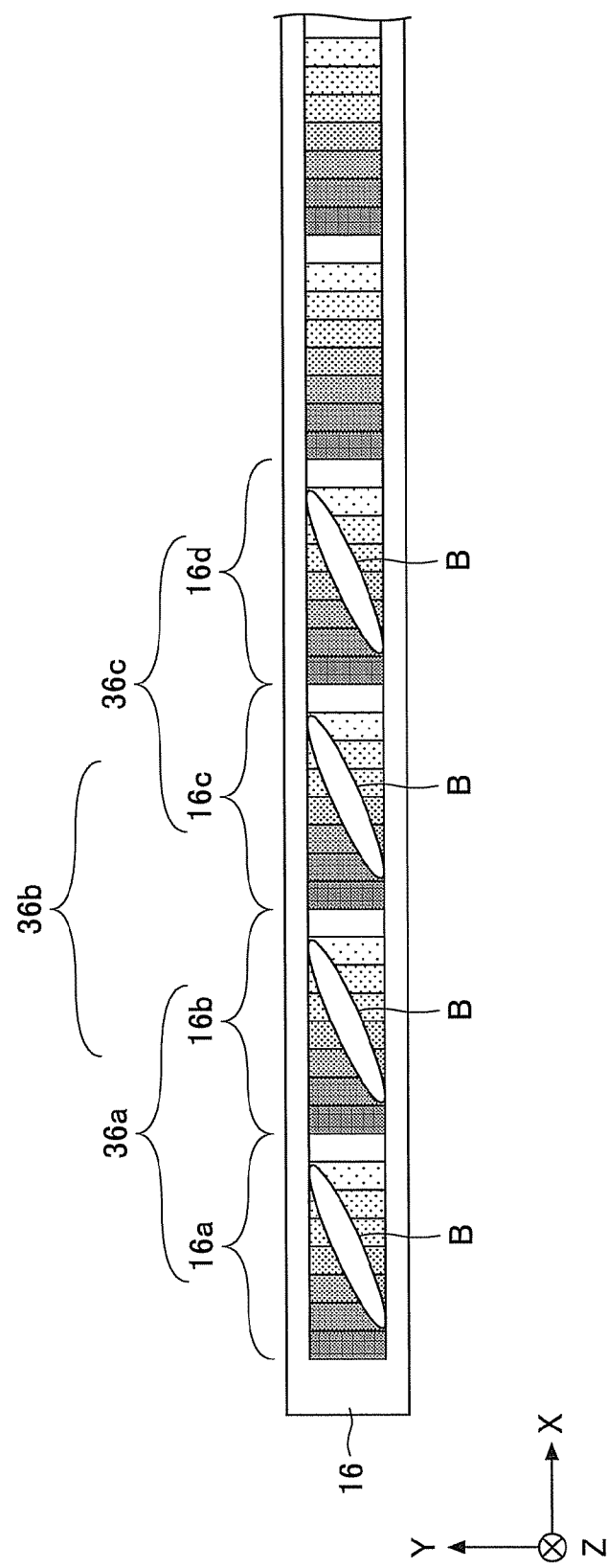
FIG. 7 is a diagram (No. 2) for illustrating an example of a spectral unit.

FIG. 7 is a diagram (No. 2) for illustrating an example of a spectroscope. In FIG. 7, two adjacent spectral sensors 16a and 16b are regarded as a spectral unit 36a. Further, two adjacent spectral sensors 16b and 16c are regarded as a spectral unit 36b. Further, two adjacent spectral sensors 16c and 16d are regarded as a spectral unit 36c. In this way, two adjacent spectral sensors are regarded as a spectral unit while the same spectral sensors are shared among the spectral units.

In other words, the spectral units are selected such that different diffraction pattern groups include common diffraction patterns. For example, the diffraction pattern group (two diffraction patterns) of the spectral unit 36a and the diffraction pattern group (two diffraction patterns) of the spectral unit 36b include a common diffraction pattern of spectral sensor 16b. It is noted that in FIG. 7 only the first-order diffraction patterns B are illustrated for the sake of convenience.

As illustrated in FIG. 7, by using the signals corresponding to the respective spectral sensors (respective diffraction patterns) in an overlapped manner while regarding the respective two adjacent spectral sensors (respective two adjacent diffraction patterns) as a corresponding one of spectral units, the same number of the spectral reflection factor data items as the case where a spectral sensor (diffraction patter) is regarded as a spectral unit can be obtained.

Of course, it is also possible to use the signals corresponding to the respective spectral sensors (respective diffraction patterns) in an overlapped manner while regarding more than two adjacent spectral sensors (more than two adjacent diffraction patterns) as a corresponding one of spectral units. An example is illustrated in FIG. 8.

Figure 8:
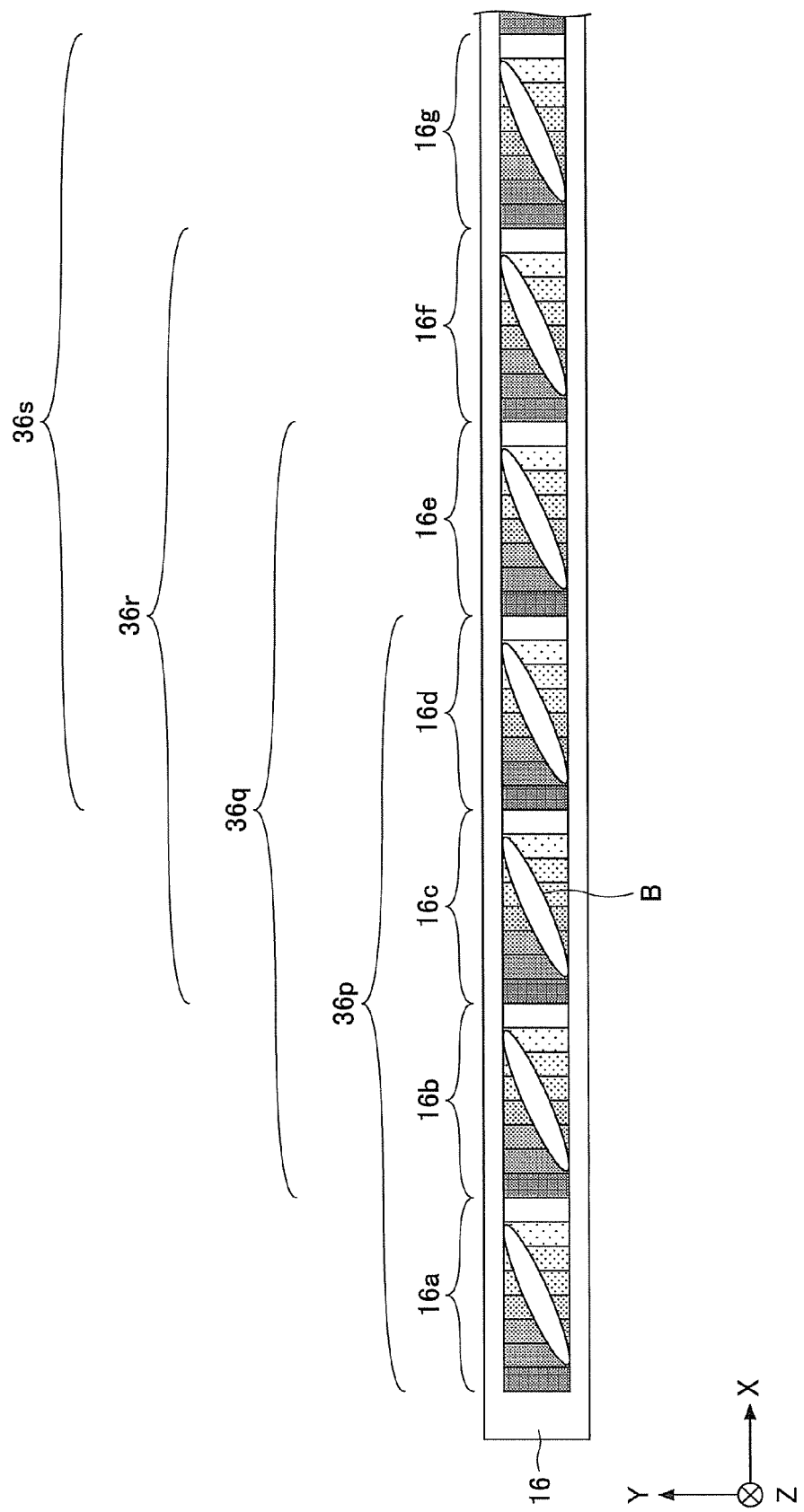
FIG. 8 is a diagram (No. 3) for illustrating an example of a spectral unit.

FIG. 8 is a diagram (No. 3) for illustrating an example of a spectroscope. In FIG. 8, four adjacent spectral sensors 16a through 16d are regarded as a spectral unit 36p. Further, four adjacent spectral sensors 16b through 16e are regarded as a spectral unit 36q. Further, four adjacent spectral sensors 16c through 16f are regarded as a spectral unit 36r. Further, four adjacent spectral sensors 16d through 16g are regarded as a spectral unit 36s. In this way, four adjacent spectral sensors (four adjacent diffraction patterns) are regarded as a spectral unit while the same spectral sensors are shared among the spectral units. It is noted that in FIG. 8 only the first-order diffraction patterns B are illustrated for the sake of convenience.

For example, it is assumed that an interval between the apertures of the hole array 13 illustrated in FIG. 1 is 1 mm, and a region (referred to as a target region, hereinafter) of four mm per side in the color chart is measured by the spectral units 36p through 36s illustrated in FIG. 8. In this case, an average spectral reflection factor of the target region can be obtained with a pitch of 1 mm.

In order to perform the precise measurement of the target region even though the position of the color chart is deviated, it is necessary to make the width of the color chart equal to the width of the target region plus the measurement pitch. In this case, since the target region is 4 mm and the measurement pitch is 1 mm, the width of the color chart may be 5 mm in order to obtain the accurate data of the region of 4 mm per side.

On the other hand, it is assumed that an interval between the apertures of the hole array 13 illustrated in FIG. 1 is 4 mm, and a region of four mm per side in the color chart is measured by the respective spectral sensors (without using the spectral unit). In this case, the spectral reflection factor of the target region can be obtained with a pitch of 4 mm. Since the target region is 4 mm and the measurement pitch is 4 mm, the width of the color chart should be 8 mm in order to obtain the accurate data of the region of 4 mm per side.

Thus, by using the same spectral sensors in an overlapped manner while regarding adjacent spectral sensors (adjacent diffraction patterns) as a corresponding one of spectral units, the width of the color chart can be reduced and thus more color charts can be placed in a certain area.

In this way, according to the first variant of the first embodiment, the same spectral sensor is shared among the spectral units. With this arrangement, it is possible to obtain average spectral reflection factors over a range which is wider than the measurement pitch (a pitch of the apertures of the hole array) using the same optical system as the case with the first embodiment. This is suited for evaluating the color chart or the like.

Second Variant of the First Embodiment

According to a second variant of the first embodiment, an example is illustrated in which the calculating part includes plural transformation matrix storing parts and plural spectral characteristic calculating parts. It is noted that in the second variant of the first embodiment an explanation for the components which are the same as those in the previously described embodiment is omitted.

Figure 9:
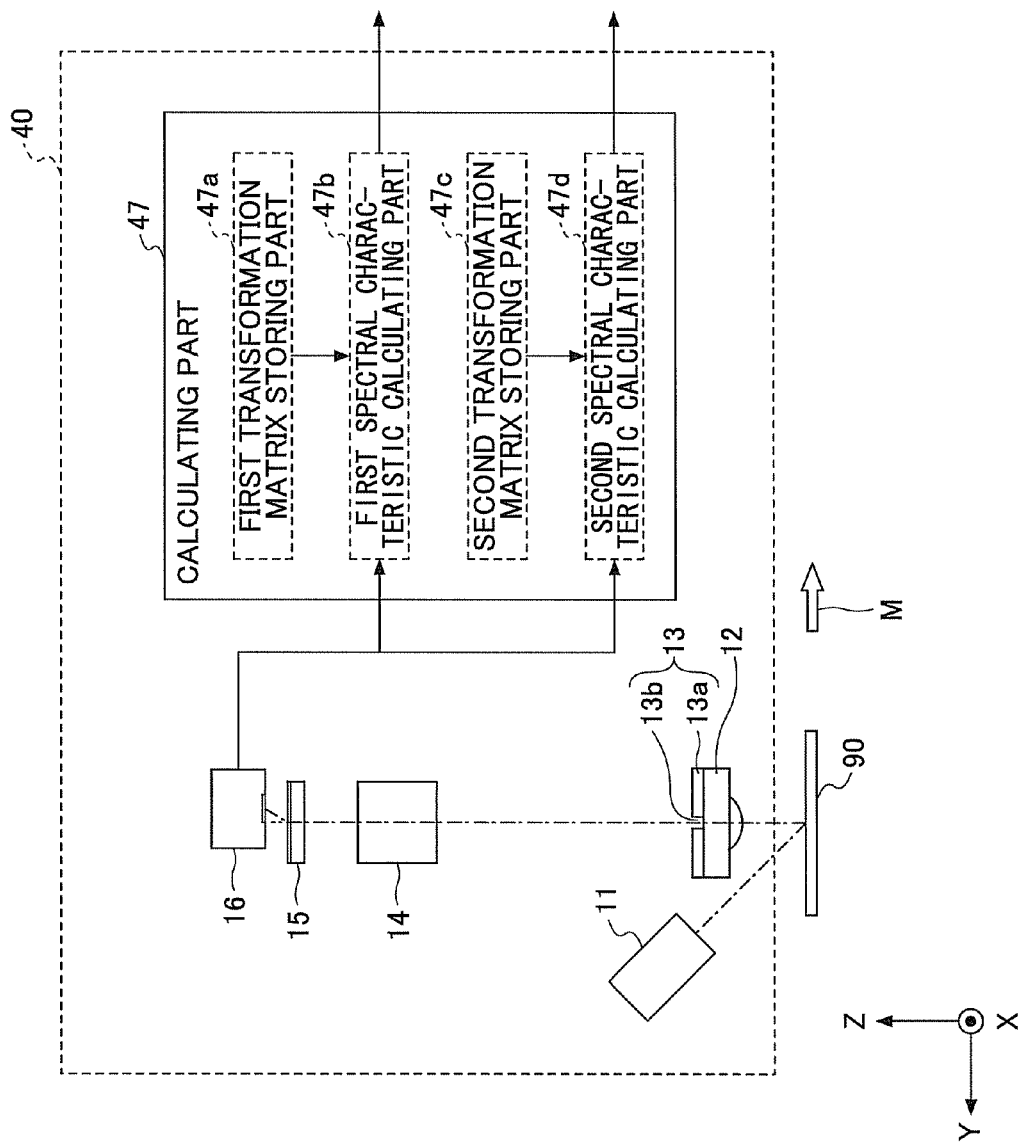
FIG. 9 is a diagram for schematically illustrating a spectral characteristic acquiring apparatus according to a second variant of the first embodiment.

FIG. 9 is a diagram for schematically illustrating a spectral characteristic acquiring apparatus according to the second variant of the first embodiment. Referring to FIG. 9, a spectral characteristic acquiring apparatus 40 differs from the spectral characteristic acquiring apparatus 10 (see FIG. 1) in that the calculating part 17 is replaced with a calculating part 47.

In the spectral characteristic acquiring apparatus 40, the diffused reflection light beams with the respective wavelengths received by the line sensor 16 are subject to optoelectronic conversion according to the received light amount, and they are digitized, for example, before they are transferred to the calculating part 47. After spectral information of the one-dimensional line is transferred to the calculating part 47, the image carrying medium 90 to be measured is moved in the direction indicated by the arrow M in FIG. 9 with respect to the spectral characteristic acquiring apparatus 40, and then spectral information of the next one-dimensional line is acquired by the line sensor 16 and transferred to the calculating part 47. By repeating such operations, the color measuring over the full width of the image is enabled.

The calculating part 47 has a function of calculating the spectral characteristics at plural locations of the image carrying medium 90 based on the electric signals output from the spectral sensors 16a, 16b, 16c, 16d, etc. The calculating part 47 includes a first transformation matrix storing part 47a, a first spectral characteristic calculating part 47b, a second transformation matrix storing part 47c, and a second spectral characteristic calculating part 47d. The calculating part 47 can be configured such that it includes a CPU, etc., for example, as is the case with the calculating part 17.

For example, the first spectral characteristic calculating part 47b calculates, based on the electric signals output from the spectral units where a spectral sensor is regarded as a spectral unit, the transformation matrix for converting the electric signals into the spectral reflection factors by performing, on a spectral unit basis (i.e., a spectral sensor basis), a multiple regression analysis in which the known spectral reflection factors are used as response variables and the electric signals are used as predictor variables. The first transformation matrix storing part 47a stores the transformation matrixes calculated by the first spectral characteristic calculating part 47b. Further, the first spectral characteristic calculating part 47b calculates products of the electrical signals output from the spectral units and the transformation matrixes of the corresponding spectral units stored in the first transformation matrix storing part 47a to calculate the spectral reflection factors of the spectral units (i.e., the spectral sensors).

On the other hand, for example, the second spectral characteristic calculating part 47d calculates, based on the electric signals output from the spectral units where adjacent two spectral sensors are regarded as a spectral unit, the transformation matrix for converting the electric signals into the spectral reflection factors by performing, on a spectral unit basis, a multiple regression analysis in which the known spectral reflection factors are used as response variables and the electric signals are used as predictor variables. The second transformation matrix storing part 47c stores the transformation matrixes calculated by the second spectral characteristic calculating part 47d. Further, the second spectral characteristic calculating part 47d calculates products of the electrical signals output from the spectral units and the transformation matrixes of the corresponding spectral units stored in the second transformation matrix storing part 47c to calculate the spectral reflection factors of the spectral units.

In this way, according to a second variant of the first embodiment, the calculating part includes plural transformation matrix storing parts and plural spectral characteristic calculating parts. With this arrangement, the transformation matrixes corresponding to the respective spectral units where a spectral sensor is regarded as a spectral unit, the transformation matrixes corresponding to the respective spectral units where adjacent two spectral sensors are regarded as a spectral unit, etc., are calculated in advance by the calibration process. Therefore, it becomes possible to acquire the spectral reflection factors of respective portions of the image on the target object with different spatial resolutions using the same optical system without changing the aperture array. In other words, part replacement which otherwise would be involved in selecting an appropriate spatial resolution according to the purpose of the measurement or the target object becomes unnecessary, and spectral characteristics suited for the purpose of the measurement or the target object can be obtained with the same hardware resources.

Further, the calculating part can be implemented by plural programs in a computer, for example, and thus spectral reflection factor data of plural spatial resolutions can be obtained with the same optical system by selecting the programs.

It is noted that the number of the spectral sensors regarded as a spectral unit may be selected as appropriate with respect to the first spectral characteristic calculating part 47b and the second spectral characteristic calculating part 47d. For example, in the first spectral characteristic calculating part 47b adjacent "a" ("a" is a natural number more than or equal to 2) spectral sensors (diffraction patterns) may be regarded as a spectral unit while in second spectral characteristic calculating part 47d adjacent "b" ("b" is different from "a" and a natural number more than or equal to 2) spectral sensors (diffraction patterns) may be regarded as a spectral unit. Further, the calculating part may include more than two transformation matrix storing parts and spectral characteristic calculating parts.

Third Variant of the First Embodiment

According to a third variant of the first embodiment, an example is illustrated in which an interval between the diffraction patterns imaged on adjacent spectral sensors is shifted from an integral multiple of an interval between the pixels of the line sensor. It is noted that in the third variant of the first embodiment an explanation for the components which are the same as those in the previously described embodiment is omitted.

Figure 10:
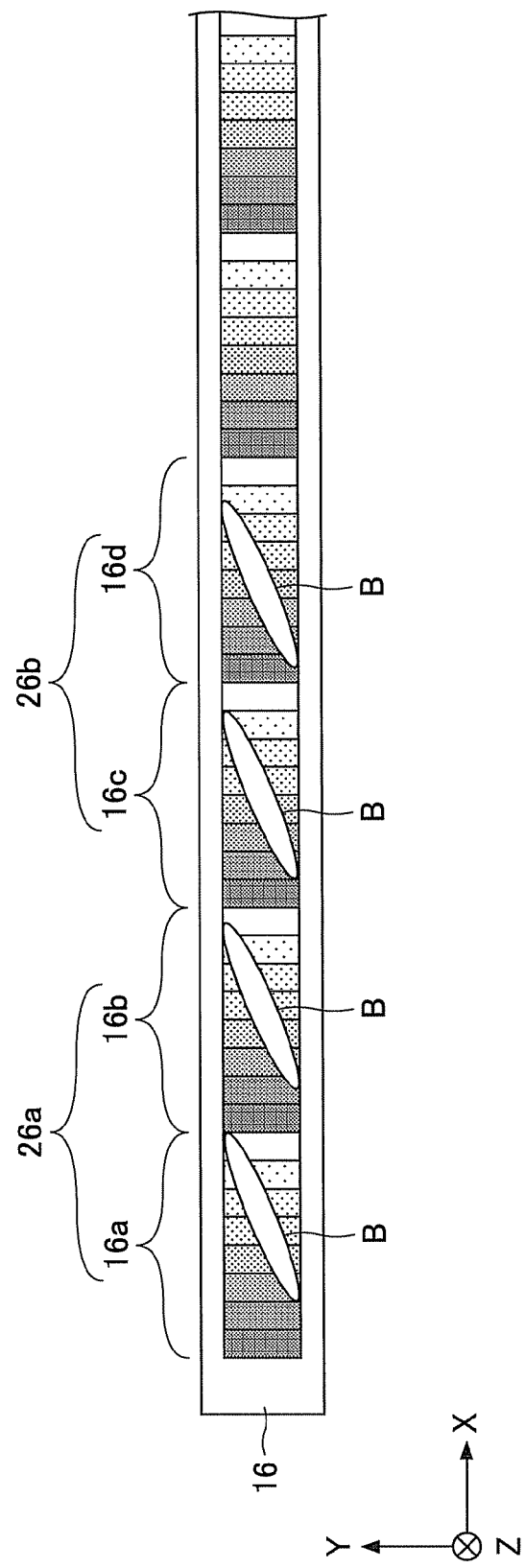
FIG. 10 is a diagram (No. 2) for illustrating a status of diffraction patterns incident on a line sensor, viewed from a side of an incident plane.

FIG. 10 is a diagram (No. 2) for illustrating a status of diffraction patterns incident on the line sensor, viewed from a side of an incident plane. Referring to FIG. 10, the number of pixels of the spectral sensors 16a through 16d is 8, and an interval between the first-order diffraction pattern B of the spectral sensor 16a and the first-order diffraction pattern B of the spectral sensor 16b is about 8½-times of the pixel width of the line sensor 16. In other words, an interval between the diffraction patterns on the line sensor 16 does not correspond to an integral multiple of an interval between the pixels of the line sensor 16. It is noted that in FIG. 10 only the first-order diffraction patterns B are illustrated for the sake of convenience.

The interval between the first-order diffraction pattern B of the spectral sensor 16a and the first-order diffraction pattern B of the spectral sensor 16b can be deviated from an integral multiple of the interval between the pixels of the line sensor 16 by adjusting an imaging magnification determined by a positional relationship between the hole array 13, the imaging optical system 14 and the line sensor 16 illustrated in FIG. 1, etc.

In the example illustrated in FIG. 10, two adjacent spectral sensors 16a and 16b (two adjacent diffraction patterns) are regarded as a spectral unit 26a, and two first-order diffraction patterns B of the spectral unit 26a are deviated by about 0.5 pixels in a relative positional relationship with respect to the pixels. For this reason, different spectral characteristics can be obtained from the spectral sensors 16a and 16b of the spectral unit 26a. As a result of this, it is possible to acquire the spectral reflection factors with high accuracy.

It is noted that in the case where adjacent three spectral sensors are regarded as a spectral unit, for example, if the number of the pixels of the spectral sensors 16a through 16d is 8, the same effect can be obtained by performing adjustment such that the intervals between the first-order diffraction patterns B of the respective spectral units are about 8.33 times of the pixel width of the line sensor 16. In this way, with respect to the signal used for estimating the spectral reflection factors, it is preferred that the signal is independent as much as possible, because the estimation accuracy becomes higher.

In this way, according to the third variant of the first embodiment, the interval between the diffraction patterns imaged on adjacent spectral sensors is deviated from an integral multiple of the interval between the pixels of the line sensor. With this arrangement, in the case where the adjacent spectral sensors are regarded as a spectral unit, different spectral characteristics can be obtained from the respective spectral sensors of the spectral unit, and thus it is possible to acquire the spectral reflection factors with high accuracy. In particular, this variant has an advantage in that the measurement accuracy can be increased in acquiring the spectral characteristics with reduced spatial resolution.

Second Embodiment

According to a second embodiment, an example is described in which an image evaluating apparatus includes the spectral characteristic acquiring apparatus. It is noted that in the second embodiment an explanation for the components which are the same as those in the previously described embodiment is omitted.

Figure 11:
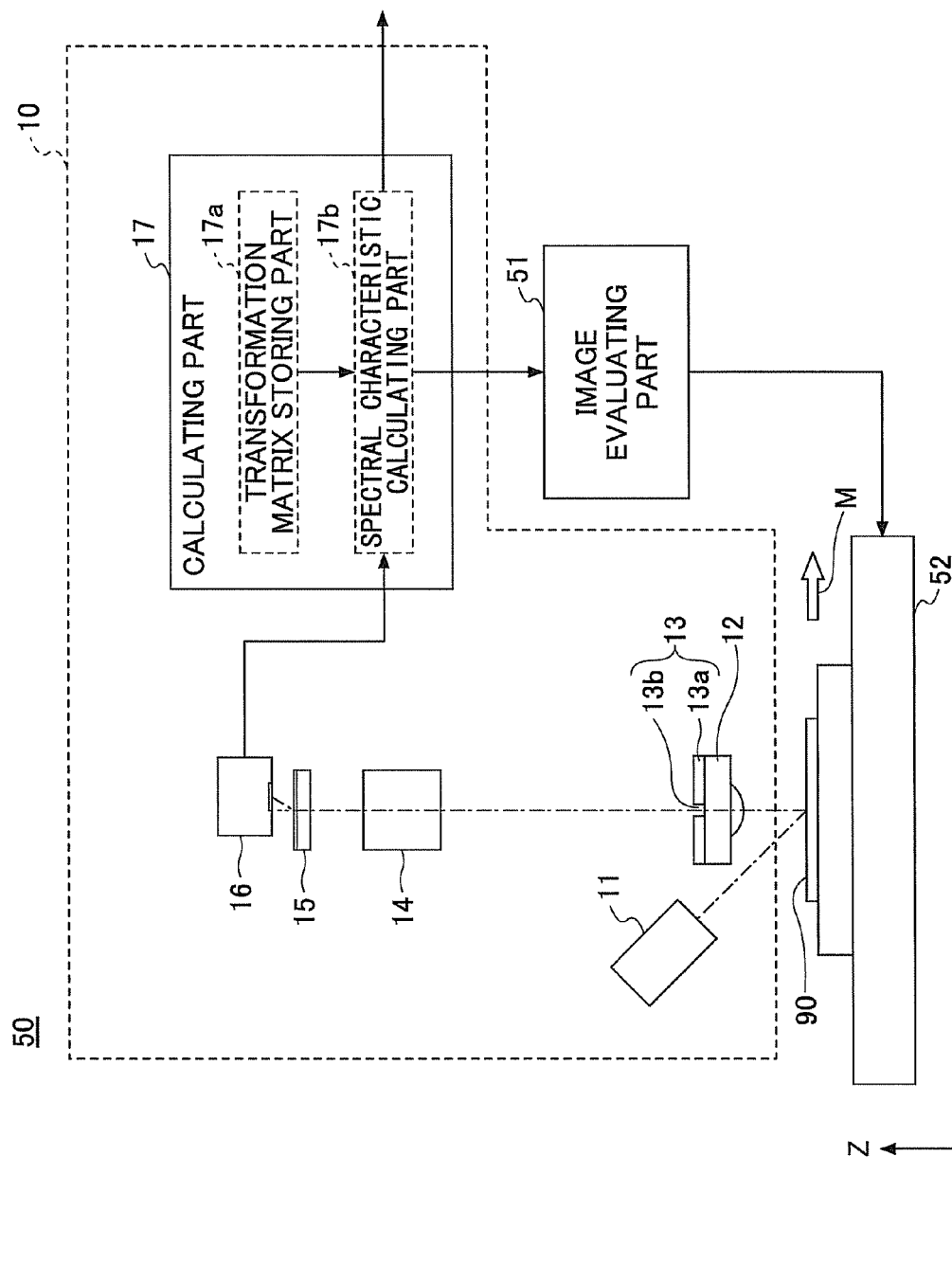
FIG. 11 is a diagram for schematically illustrating an image evaluating apparatus according to a second embodiment.

FIG. 11 is a diagram for schematically illustrating an image evaluating apparatus according to the second embodiment. Referring to FIG. 11, the image evaluating apparatus 50 measures an image over the full width of the image, which image is formed on the image carrying medium 90 by an electrophotographic image forming apparatus or the like, for example. The image evaluating apparatus includes the spectral characteristic acquiring apparatus 10 illustrated in FIG. 1, an image evaluating part 51 and a conveyer 52. It is noted that plural spectral characteristic acquiring apparatuses 10 may be arranged in parallel in an X-direction such that the target object of a larger size can be measured.

The image evaluating part 51 has a function of controlling the conveyer 52 to convey the image carrying medium 90, which is the target object to be measured, at a predetermined speed in a direction indicated by an arrow M. Further, the image evaluating part 51 has a function of acquiring the spectral characteristics of the image carrying medium 90 with the spectral characteristic acquiring apparatus 10 in synchronization with the conveyance of the image carrying medium 90 with the conveyer 52, and evaluating the color of the image formed in plural colors on the image carrying medium 90. The image evaluating part 51 is capable of calculating CIELAB value or the like which indicates the color of a reflector, for example.

Further, the image evaluating part 51 has a function of storing the spectral reflection factors of portions of a reference object, and a function of comparing the spectral reflection factors of the reference object with the spectral reflection factors of the target object to be examined, and displaying the portion which has a great difference, etc. The image evaluating part 51 is capable of examining the image of the target object (image carrying medium 90) according to an instruction from an operator.

The image evaluating part 51 includes a CPU, a ROM, a main memory, etc., for example, and the functions of the image evaluating part 51 are implemented when programs stored in the ROM are read out from the main memory and then executed by the CPU. However, a part or all of the image evaluating part 51 may be implemented by only hardware resources. Further, the image evaluating part 51 may include plural apparatuses which are physically separated.

It is noted that in the image evaluating apparatus 50 the spectral characteristic acquiring apparatus 40 may be used instead of the spectral characteristic acquiring apparatus 10.

In this way, according to the second embodiment, since the image evaluating apparatus includes the spectral characteristic acquiring apparatus according to the first embodiment, and thus the spectral characteristics of the respective portions of the image on the image carrying medium can be measured with different spatial resolutions using the same optical system, it is possible to appropriately evaluate the spectral characteristics according to target features of the target object. For example, it is possible to evaluate the spectral reflection factors of a narrow portion with high spatial resolution, or evaluate the spectral reflection factors of a portion such as the color chart whose area is great to some degree with high accuracy.

Third Embodiment

According to a third embodiment, an example is described in which an image forming apparatus includes the image evaluating apparatus according to the second embodiment. It is noted that in the third embodiment an explanation for the components which are the same as those in the previously described embodiment is omitted.

Figure 12:
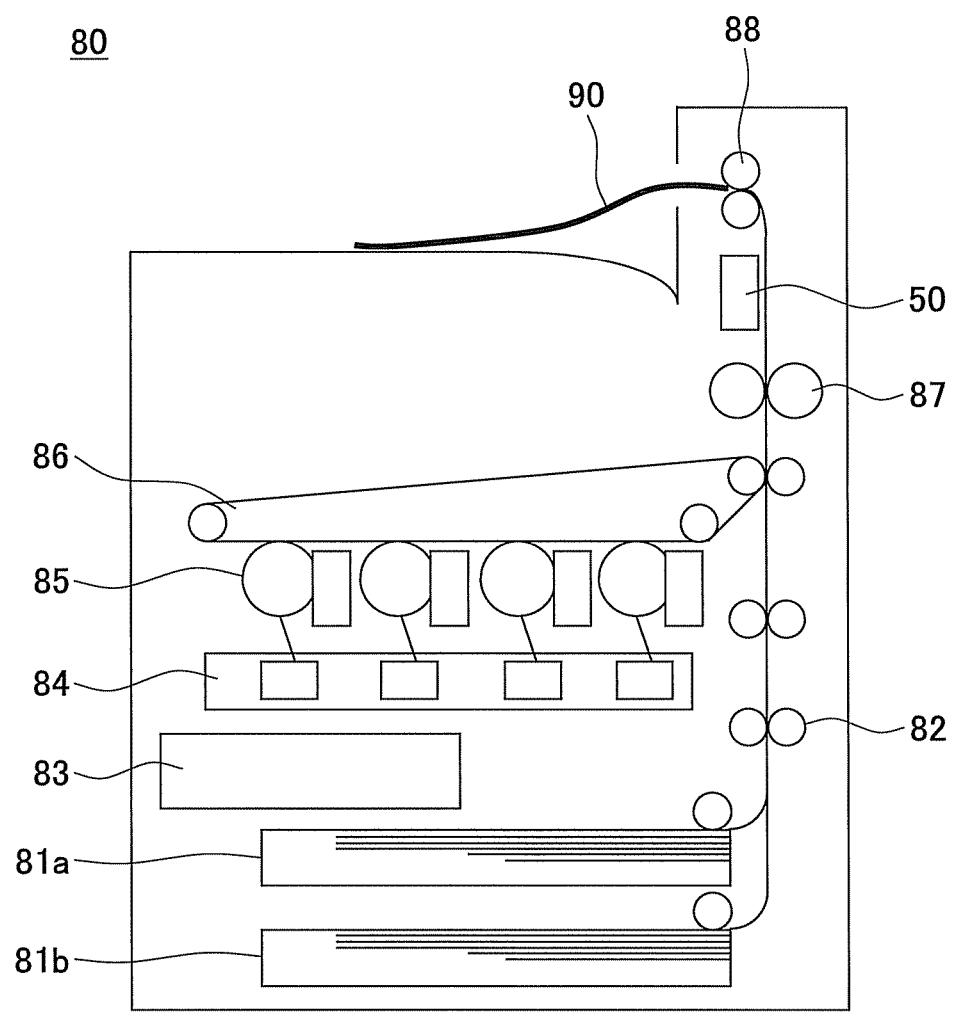
FIG. 12 is a diagram for schematically illustrating an image evaluating apparatus according to a third embodiment.

FIG. 12 is a diagram for schematically illustrating an image forming apparatus according to the third embodiment. Referring to FIG. 12, the image forming apparatus 80 includes the image evaluating apparatus 50 according to the second embodiment, a paper feed cassette 81a, a paper feed cassette 81b, paper feed rollers 82, a controller 83, a scanning optical system 84, photosensitive bodies 85, an intermediate transfer body 86, a fuser roller and an ejecting roller 88. An image carrying medium (such as a paper) is indicated by a reference numeral 90.

In the image forming apparatus 80, the image carrying medium 90 is conveyed by a guide (not illustrated) and the paper feed rollers 82 from the paper feed cassette 81a or the paper feed cassette 81b, the photosensitive bodies 85 are exposed by the scanning optical system 84, and color pigments are applied for the development. The developed images are transferred to and superposed on the intermediate transfer body 86 and then the superposed image in transferred from the intermediate transfer body 86 to the image carrying medium 90. The image transferred to the image carrying medium 90 is fused by the fuser roller 87, and the image carrying medium 90 having the image formed thereon is ejected by the ejecting roller 87. The image evaluating apparatus 50 is arranged after the fuser roller 87.

In this way, according to the third embodiment, by installing the image evaluating apparatus according to the second embodiment at a predetermined location, color information in a plane of the image carrying medium can be acquired in a two-dimensional manner in synchronization with the conveyance of the image carrying medium. If the image forming apparatus 80 is of an electrophotographic type, for example, irregular colors in the plane of the image carrying medium can be reduced by performing image processing such as gamma correction prior to the printing or control of a light source of a writing scanning optical system within a one-time scanning operation, based on the two-dimensional color information.

Further, if the image forming apparatus 80 is of an inkjet type, for example, irregular colors in the plane of the image carrying medium can be reduced by directly controlling an ink discharge amount according to the head position.

Further, since the image evaluating apparatus 50 according to the second embodiment enables acquiring the spectral characteristics with different spatial resolutions over the whole plane of the image in a two-dimensional manner, the evaluation of the spectral characteristics adequate for the color chart in the case where there is the color chart and the evaluation of the spectral characteristics adequate for an arbitrary location of an arbitrary image of a user where there is no color chart are possible. Then, by performing the adjustment of the process based on the respective evaluation result, the image forming apparatus with increased color stability and increased color reproduction capability can be implemented.

The preferred embodiments and variants thereof are described above in detail. However, it should be understood that the present invention is not limited to the above-described embodiments, and other embodiments, variations thereof, addition and elimination may be made within the scope contemplated by those skilled in the art.

The present application is based on Japanese Priority Application No. 2011-198374, filed on Sep. 12, 2011, the entire contents of which are hereby incorporated by reference.

What is claimed is:

1. A spectral characteristic acquiring apparatus, comprising:
an area dividing part that divides a reflected light beam into plural areas with plural apertures, the reflected light beam being generated based on a light beam radiated from a light radiating part to an image carrying medium;
a spectrum separating part that performs a spectrum separation of the reflected light beams divided by the area dividing part to form plural diffraction patterns;
a light receiving part that receives the diffraction patterns formed by the spectrum separating part with plural pixels to convert the received diffraction patterns into electrical signals; and
a calculating part that calculates, based on the electrical signals, a spectral characteristic that indicates a ratio of a light amount of the reflected light beam at plural locations of the image carrying medium, wherein
the calculating part includes
a transformation matrix storing part that stores a transformation matrix used for calculating the spectral characteristic corresponding to the electrical signals of a first diffraction pattern group including two or more adjacent diffraction patterns,
a spectral characteristic calculating part that calculates, based on the electrical signals of the first diffraction pattern group and the corresponding transformation matrix, the spectral characteristic at the locations of the image carrying medium corresponding to the apertures of the first diffraction pattern group,
a second transformation matrix storing part that stores a second transformation matrix used for calculating the spectral characteristic associated with the electrical signals of a second diffraction pattern group including two or more adjacent diffraction patterns, the number of the adjacent diffraction patterns included in the second diffraction pattern group being different from the number of the adjacent diffraction patterns included in the first diffraction pattern group; and
a second spectral characteristic calculating part that calculates, based on the electrical signals of the second diffraction pattern group and the corresponding second transformation matrix, the spectral characteristic at the locations of the image carrying medium corresponding to the apertures of the second diffraction pattern group.

2. The spectral characteristic acquiring apparatus of claim 1, wherein the transformation matrix storing part stores plural transformation matrixes including said transformation matrix, each of the transformation matrixes is used for calculating the spectral characteristic corresponding to the electrical signals of each of plural first diffraction pattern groups including said first diffraction pattern group, and the first diffraction pattern groups include one first diffraction pattern group and another first diffraction pattern group that include a common diffraction pattern.

3. The spectral characteristic acquiring apparatus of claim 1, further comprising:
a first imaging part that collects the reflected light beam to form an image on the area dividing part; and
a second imaging part that collects the reflected light beams divided into the areas by the area dividing part to form images on the spectrum separating part, wherein
a positional relationship between the area dividing part, the second imaging part and the light receiving part is configured such that an interval between the diffraction patterns on the image carrying medium does not correspond to an integral multiple of an interval between the pixels of the light receiving part.

4. The spectral characteristic acquiring apparatus of claim 1, wherein the calculating part further includes
a third transformation matrix storing part that stores third transformation matrixes used for calculating the spectral characteristics associated with the electrical signals of the respective diffraction patterns; and
a third spectral characteristic calculating part that calculates, based on the electrical signals of the respective diffraction patterns and the corresponding third transformation matrixes, the spectral characteristics at the locations of the image carrying medium corresponding to the apertures of the respective diffraction patterns.

5. An image evaluating apparatus, comprising:
a spectral characteristic acquiring apparatus that includes
an area dividing part that divides a reflected light beam into plural areas with plural apertures, the reflected light beam being generated based on a light beam radiated from a light radiating part to an image carrying medium,
a spectrum separating part that performs a spectrum separation of the reflected light beams divided by the area dividing part to form plural diffraction patterns,
a light receiving part that receives the diffraction patterns formed by the spectrum separating part with plural pixels to convert the received diffraction patterns into electrical signals, and
a calculating part that calculates, based on the electrical signals, a spectral characteristic that indicates a ratio of a light amount of the reflected light beam at plural locations of the image carrying medium, wherein
the calculating part includes
a transformation matrix storing part that stores a transformation matrix used for calculating the spectral characteristic corresponding to the electrical signals of a first diffraction pattern group including two or more adjacent diffraction patterns,
a spectral characteristic calculating part that calculates, based on the electrical signals of the first diffraction pattern group and the corresponding transformation matrix, the spectral characteristic at the locations of the image carrying medium corresponding to the apertures of the first diffraction pattern group,
a second transformation matrix storing part that stores a second transformation matrix used for calculating the spectral characteristic associated with the electrical signals of a second diffraction pattern group including two or more adjacent diffraction patterns, the number of the adjacent diffraction patterns included in the second diffraction pattern group being different from the number of the adjacent diffraction patterns included in the first diffraction pattern group; and
a second spectral characteristic calculating part that calculates, based on the electrical signals of the second diffraction pattern group and the corresponding second transformation matrix, the spectral characteristic at the locations of the image carrying medium corresponding to the apertures of the second diffraction pattern group
a conveyer that conveys the image carrying medium; and
an image evaluating part that acquires the spectral characteristic from the spectral characteristic acquiring apparatus in synchronization with a conveyance of the image carrying medium on the conveyer, and evaluates, based on the spectral characteristic acquired by the spectral characteristic acquiring apparatus, a color of the image formed with plural colors on the image carrying medium.

6. A spectral characteristic acquiring method, comprising:
dividing, with an area dividing part, a reflected light beam into plural areas with plural apertures, the reflected light beam being generated based on a light beam radiated from a light radiating part to an image carrying medium;
performing, with a spectrum separating part, a spectrum separation of the reflected light beams divided by the area dividing part to form plural diffraction patterns;
receiving, with a light receiving part, the diffraction patterns formed by the spectrum separating part with plural pixels to convert the received diffraction patterns into electrical signals, and
calculating, with a calculating part, based on the electrical signals, a spectral characteristic that indicates a ratio of a light amount of the reflected light beam at plural locations of the image carrying medium, wherein
the calculating includes calculating, based on the electrical signals of a first diffraction pattern group and a transformation matrix, the spectral characteristic at the locations of the image carrying medium corresponding to the apertures of the first diffraction pattern group, wherein the first diffraction pattern group includes two or more adjacent diffraction patterns, and the transformation matrix is used for calculating the spectral characteristic corresponding to the electrical signals of the first diffraction pattern group, and
calculating, based on the electrical signals of a second diffraction pattern group and a second transformation matrix, the spectral characteristic at the locations of the image carrying medium corresponding to the apertures of the second diffraction pattern group, wherein the second diffraction pattern group includes two or more adjacent diffraction patterns, the number of the adjacent diffraction patterns included in the second diffraction pattern group being different from the number of the adjacent diffraction patterns included in the first diffraction pattern group, and the second transformation matrix is used for calculating the spectral characteristic corresponding to the electrical signals of the second diffraction pattern group.

7. The spectral characteristic acquiring method of claim 6, wherein the calculating further includes calculating, based on the electrical signals of the respective diffraction patterns and third transformation matrixes, the spectral characteristics at the locations of the image carrying medium corresponding to the apertures of the respective diffraction patterns, wherein the third transformation matrixes are used for calculating the spectral characteristics associated with the electrical signals of the respective diffraction patterns.

8. The spectral characteristic acquiring method of claim 6, further comprising:
collecting, with a first imaging part, the reflected light beam to form an image on the area dividing part, the correcting the reflected light beam being performed before dividing the reflected light beam into plural areas; and
collecting, with a second imaging part, the reflected light beams divided into the areas by the area dividing part to form images on the spectrum separating part, the collecting the reflected light beams divided into the areas being performed after dividing the reflected light beam into plural areas and before performing the spectrum separation.

* * * * *